United States Patent [19]

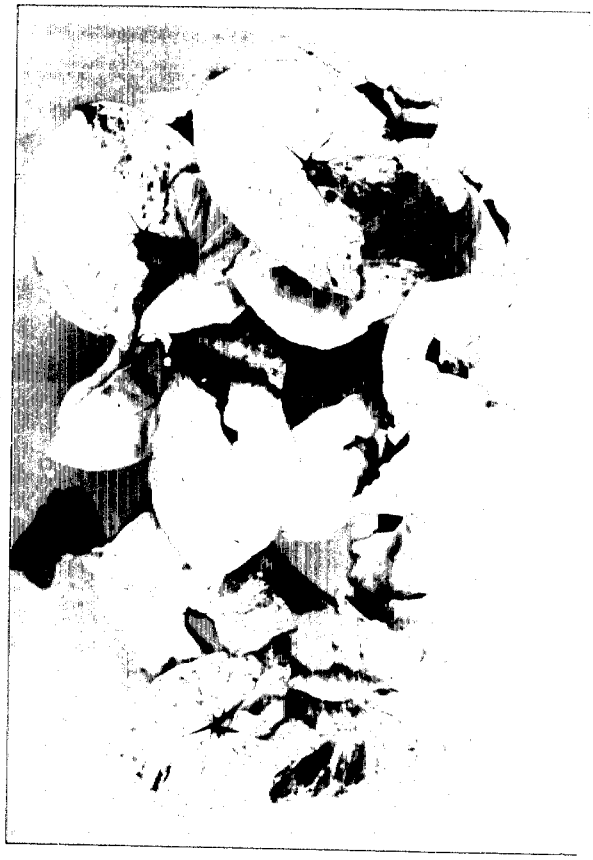

Kallert

[11] Patent Number: Plant 5,807

[45] Date of Patent: Nov. 18, 1986

[54] *SYNGONIUM PODOPHYLLUM* PLANT CV. 'JENNY KALLERT'

[76] Inventor: Günter Kallert, 2039 N. Bay Rd., Miami Beach, Fla. 33140

[21] Appl. No.: 752,800

[22] Filed: Jul. 8, 1985

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Frank B. Robb

[57] ABSTRACT

A vegetative mutant of *Syngonium podophyllum* "White Butterfly" which is of compact growth, more round leaves which are two to three times the size of the parent, petioles two to three times as large, thicker light green leaves, the leaves being most distinctly different as to color as a sort of gray, frosty green and interesting patterns of variegation where such is present.

1 Drawing Figure

GENERAL BACKGROUND AND FEATURES OF THE INVENTION

The present invention relates to a *Syngonium podophyllum* plant which I discovered some time ago growing as a vegatative mutant in my greenhouse in Miami, Fla., the parent being the unpatented Syngonium variety known as "White Butterfly".

Probably the most outstanding and different aspect of the variety of my invention, is the very distinctive color of a sort of gray, frosty green, the term being adopted by me as a basis of distinction and to identify the same as well as differentiate the plant from the parent variety which is entirely different in many aspects, since my new variety has the outstanding features to be enumerated hereinafter.

By way of identification, I have chosen to call my new variety "Jenny Kallert", recognizing that in the trade it will probably become known as "Jenny" very likely, although I will use both names as distinctive and to identify and carry forward the knowledge that the origin of the plant is and was in my greenhouse in Miami, Fla.

It may be noted that while the Syngonium podophyllum are in fact somewhat like the nephthytis plants such as those shown in U.S. Plant Pat. 763, the variety of my particular disclosure is much more compact in growth and the leaves are more round being about twice as large with a green of a very different color and the veins likewise being substantially different in color.

Further the variety which I denominate as "Jenny Kallert", is distinguished from the Syngonium "White Butterfly", its parent, by more compact growth habit, petioles which are about twice as long, and leaves which are two to three times as large, much thicker, and a lighter green and where variegated of a substantially different variegation pattern.

I have caused the variety of my invention to be propagated by asexual reproduction both from stem cuttings and through tissue culture, finding that the plant of my invention retains its distinguishing characteristics which have been noted hereinbefore.

In order to further illustrate the differences in my new variety, I provide herewith a drawing which shows a typical plant of my new variety, with color terminology from the Limit Color Cascade of Munsell Color Company and where that terminology is applicable, so used but where general terms used in the description of color in the plant and dictionary terms are suitable those terms are used in fact.

While the colors set forth are those which find their nearest counterpart in the Limit Color Cascade, the fact is that there is no particular color in such cascade which is identical to that of my variety "Jenny Kallert". However, it is obvious that by extrapolation, the colors may be distinguished and described in relation to the numerical designations set forth in the cascade, with it being borne in mind that the drawing does in fact show the plant as it appears, and the description made in a greenhouse atmosphere and light, the grayness which seems to be pervasive, being one of the distinctive aspects along with the rather frosty green color which I have chosen to demoninate the same and distinguish the same with in reference to this new variety.

With the foregoing in mind, there follows a detailed description of my new variety, and certain distinguishing aspects being noted as the description proceeds along the following lines:

PLANT

Form: A dense, compact plant, eventually becoming creeping or a vine. It is suitable for containers, hanging baskets, and totem poles.

Roots: Develop at nodes and will attach to most surfaces.

Stem: $\frac{3}{8}''$ to $\frac{1}{2}''$ in diameter, smooth, and firm.

Internodes: Average length — 2" to 3".

FOLIAGE

Size:

*Width.*—4" to 6".

*Length.*—6" to 8".

Quantity: Abundant.

Shape: Arrowhead; the base of the leaf is sagittate and the apex is cuspidate.

Texture:

*Upper surface.*—Slightly rough and bullate.

*Lower surface.*—Smooth and bullate. The leaves have a thick, succulent quality to them.

Color:

*Upper leaf surface.*—Most leaves are a pole green between 19-1 and 19-2 with some grayness and show no variegation. A few of the leaves are pale green with markings of darker green 20-13 around the edges of the leaf and as small patches on the leaves between veins. Still others have green main veins 22-11 with all areas between them darker green 22-12. There are usually and practically in all cases observed no yellow, white, or metallic markings on the leaves.

*Lower leaf surface.*—A uniform medium green 21-10.

Veins: Light green 21-1.

Petioles: Size — 4" to 6" long and ¼" to ½" in diameter.

Flowers: None.

Disease Resistance: No diseases have been observed on plants of "Jenny Kallert" grown for three years in greenhouse at Miami, Fla.

In summary, it may be noted that the peculiar green color of the plant of my new variety is in fact very distinctive and not known in the *Syngonium podophyllum* variety previously as far as I am aware.

I claim:

1. A new and distinct variety of Syngonium plant, substantially as herein shown and described, characterized particularly as to novelty by the unique combination of distinctive pale green somewhat grayish color of its leaves, more compact growth habit, more round, nearly twice as long leaves and petioles than "White Butterfly" (unpatented), the leaves also being thicker and lighter green, less and different variegation where appearing, and lack of susceptibility to any known disease.

* * * * *